(12) United States Patent
Jubin, Jr. et al.

(10) Patent No.: US 7,645,892 B2
(45) Date of Patent: Jan. 12, 2010

(54) REACTION SYSTEM

(75) Inventors: John C. Jubin, Jr., West Chester, PA (US); Wilson H. Onimus, Holmes, PA (US)

(73) Assignee: Lyondell Chemical Technology, L.P., Greenville, DE (US)

( * ) Notice: Subject to any disclaimer, the term of this patent is extended or adjusted under 35 U.S.C. 154(b) by 271 days.

(21) Appl. No.: 11/415,598

(22) Filed: May 2, 2006

(65) Prior Publication Data

US 2007/0260075 A1  Nov. 8, 2007

(51) Int. Cl.
*C07D 301/06* (2006.01)

(52) U.S. Cl. .................. 549/533; 261/114.1; 422/189; 502/242

(58) Field of Classification Search ........... 549/533; 502/245, 242, 243, 349; 261/114.1, 114.3; 422/189, 190, 191; 423/659, 588
See application file for complete search history.

(56) References Cited

U.S. PATENT DOCUMENTS

| 6,334,985 | B1 | 1/2002 | Raghuram et al. |
| 6,375,921 | B1 | 4/2002 | Eickhoff et al. |
| 6,710,192 | B2 | 3/2004 | Hancu et al. ............... 549/512 |
| 6,710,194 | B1 | 3/2004 | Cochran et al. ............ 549/533 |
| 6,867,312 | B1 | 3/2005 | Jubin, Jr. et al. ........... 549/523 |
| 2004/0124140 | A1 | 7/2004 | Sawyer et al. |
| 2004/0219080 | A1 | 11/2004 | Bilardello et al. |

FOREIGN PATENT DOCUMENTS

| DE | 948781 C | 9/1956 |
| DE | 958020 C | 2/1957 |
| JP | 4-352771 | 12/1992 |
| WO | WO2005/049194 | 6/2005 |
| WO | WO 2006/097904 | 9/2006 |
| WO | WO 2006/097905 | 9/2006 |
| WO | WO 2006/097906 | 9/2006 |

*Primary Examiner*—Bernard Dentz
*Assistant Examiner*—David E Gallis
(74) *Attorney, Agent, or Firm*—Yuanzhang Han

(57) ABSTRACT

Reaction gases such as hydrogen, oxygen and propylene are reacted in a slurry of solid catalyst in solvent, the reaction being carried out in a series of separate zones with intermediate removal of the exothermic heat of reaction by indirect heat exchange.

4 Claims, 2 Drawing Sheets

REACTION SYSTEM

BACKGROUND OF THE INVENTION

1. Field of the Invention

The present invention relates to the improved reaction of gas phase reagents in a liquid which contains slurried solid catalyst particles. The invention is especially useful for the production of propylene oxide by reaction of propylene, oxygen and hydrogen in a slurry of noble metal promoted TS-1.

2. Description of the Prior Art

The production of propylene oxide by reaction of propylene, oxygen and hydrogen using a solid noble metal promoted TS-1 catalyst is by now, well known. See for example, Japanese Kokai No. 4-352771, U.S. Pat. No. 6,867,312, U.S. Pat. No. 6,710,192, U.S. Pat. No. 6,710,194 and the like.

It is often advantageous to carry out the reaction by contacting gaseous reactants in a slurry of solid catalyst particles in a suitable liquid such as methanol or methanol and water mixtures.

In such systems, for economic operation it is important that high reaction rates be maintained as well as high reaction selectivities to propylene oxide. It is also important that attrition of the slurried solid catalyst be maintained at a low level since excessive catalyst attrition causes operational problems and requires more frequent catalyst replacement.

Since the reaction is exothermic, it is also important that heat of reaction be efficiently removed from the reaction zone.

BRIEF DESCRIPTION OF THE INVENTION

In accordance with the present invention an improved reaction process and system is provided for the production of propylene oxide whereby high reaction rates and selectivities are maintained while low rates of catalyst attrition are achieved. A tower reactor is provided which has a plurality of separate reaction zones wherein the reactant gases are reacted in a slurry of catalyst particles in appropriate solvent. Heat removal zones are provided between the reaction zones in order that heat of reaction can efficiently be removed by indirect heat transfer. Each of the reaction zones is suitable for propylene oxide production by reacting propylene, oxygen and hydrogen reactant gases in a liquid medium comprised of a slurry of catalyst particles in a solvent such as methanol or methanol and water. The composition of the reaction mixture can be separately controlled in each of the separate reaction zones to give improved product selectivity. The reaction slurry mixture passes from each of the separate reaction zones to a shell and tube cooling zone which is provided with a plurality of tubes through which the reaction mixture passes, while on the shell side an appropriate coolant is provided to remove reaction heat. A perforated plate having special hole size and spacing is provided to ensure that the mixture of gaseous reactants is introduced to the reaction zone as finely divided bubbles.

BRIEF DESCRIPTION OF THE DRAWINGS

The accompanying drawings illustrate the invention. FIG. 1 illustrates the overall process while

DETAILED DESCRIPTION

Figure 1:
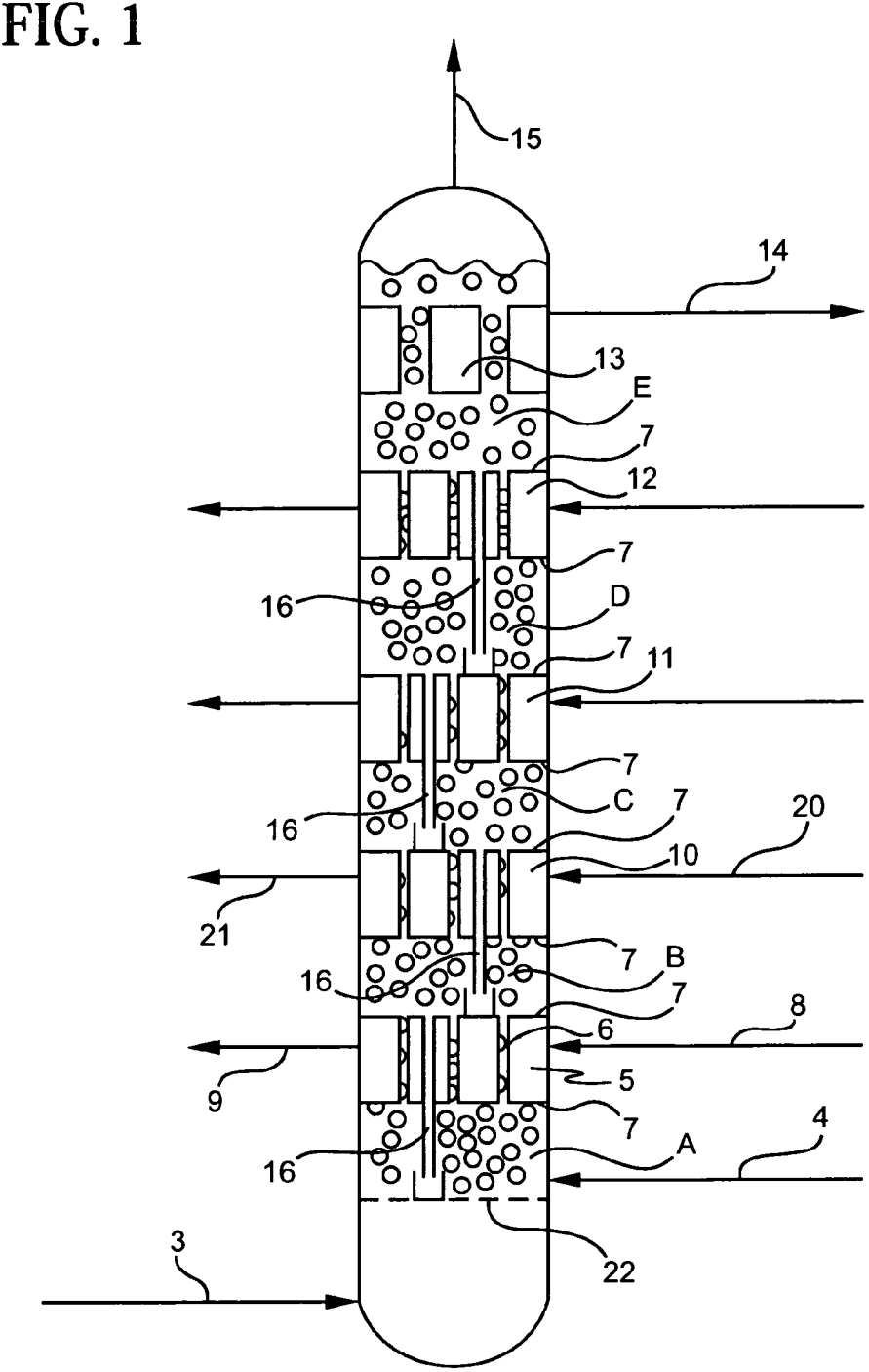

Referring to FIG. 1, reactor 1 is a tower reactor which, as shown, has 5 reaction zones, zones A-E. As depicted, oxygen, hydrogen, propylene and recycle gases are introduced via line 3 and the solvent is introduced via line 4. An inventory of catalyst is retained in the reactor. In zone A as in the other reaction zones agitation is provided by the flow of reaction gases and solvent slurry, and perforated plate 22 is provided to provide small discrete bubbles of reaction gases to the reaction. The solvent is introduced above the perforated plate 22.

From reaction zone A both gases and liquid containing the slurried catalyst pass upwardly to heat removal zone 5. In zone 5, slurry and bubbles of gases from reaction zone A pass upwardly through a plurality of tubes 6 which are mounted in place by tube sheets 7. A coolant such as water is introduced to the shell side of the tubes 6 via line 8 and by indirect heat exchange the coolant removes the heat generated by the reaction in zone A, the coolant passing from zone 5 via line 9.

The reaction mixture and reactants pass through tubes 6 through zone 5 to the next reaction zone B where further reaction takes place. The reaction mixture passes from reaction zone B to cooling zone 10 where reaction heat is removed, then to reaction zone C, cooling zone 11, reaction zone D, cooling zone 12 and reaction zone E. From zone E the reaction liquid is separated from solid catalyst by filter tubes 13, the reaction liquid passing via line 14 to appropriate separation means for product recovery and solvent recycle. Vapors are recovered from reactor 1 via line 15.

In each reaction zone, except for the lowest, means 16, which preferably are suitable tubes, are provided for recycling entrained slurry to the next lower reaction zone. In each cooling zone the tubes through which the reaction mixture passes are of a size and number to ensure that reaction heat is readily removed. Water is the preferred coolant although other coolants can be used. Flow velocity of the reaction mixture through the tubes is illustratively 3-6 ft/sec to minimize catalyst attrition.

The catalyst which is employed in the present invention is suitably a noble metal promoted TS-1 catalyst, although such other solid catalysts which are effective for the reaction can be used.

The preparation of TS-1 by hydrothermal crystallization is by now well known and the preparation techniques previously used can be employed to prepare catalyst for use in this invention.

Titanium zeolite synthesis typically comprises reacting a titanium compound, a silicon source, and a templating agent at a temperature and for a time sufficient to form a titanium zeolite. Suitable titanium compounds useful in titanium zeolite synthesis include, but are not limited to, titanium alkoxides and titanium halides. Preferred titanium alkoxides are titanium tetraisopropoxide, titanium tetraethoxide and titanium tetrabutoxide. Titanium tetraethoxide is especially preferred. Preferred titanium halides include titanium trichloride and titanium tetrachloride.

Suitable silicon sources include, but are not limited to, colloidal silica, fumed silica and silicon alkoxides. Preferred silicon alkoxides are tetraethylorthosilicate, tetramethylorthosilicate, and the like.

Tetraethylorthosilicate is especially preferred.

The templating agent used in crystal synthesis is typically a tetraalkylammonium cation, particularly tetrapropylammonium cation. The templating agent is typically used in the zeolite synthesis as a templating agent compound consisting of the templating agent and an anionic species. The tetraalkylammonium cation is typically used as a hydroxide, halide, nitrate, acetate, and the like compound. Tetraalkylammonium hydroxides and tetraalkylammonium halides, such as tetrapropylammonium hydroxide tetrapropylammonium halide, are preferred templating agent compounds.

Tetrapropylammonium hydroxide is especially preferred.

Synthesis of titanium zeolites is carried out by a hydrothermal crystallization of a reaction mixture prepared by combining the titanium compound, silicon source, and templating agent compound is the presence of water. Other solvents such as alcohols may also be present. Alcohols such as isopropyl, ethyl and methyl alcohol are preferred, and isopropyl alcohol is especially preferred.

Generally, the hydrothermal process used to prepare titanium zeolites involves forming a reaction mixture wherein the molar ratios of additives (as defined in terms of moles of templating agent, moles of $SiO_2$ and moles of $TiO_2$) comprise the following molar ratios: $TiO_2:SiO_2$=0.5-5:100; and templating agent: $SiO_2$=10-50:100. The water: $SiO_2$ molar ratio is typically from about 1000-5000:100 and the solvent: $SiO_2$ molar ratio may be in the range of 0-500:100.

The reaction mixture is prepared by mixing the desired sources of titanium, silicon and templating agent compound to give the reaction mixture. It is also typically necessary that the mixture have a pH of about 9 to about 13. The basicity of the mixture is controlled by the amount of templating agent compound (it is in the hydroxide form) which is added and the use of other basic compounds. To increase the basicity of the mixture, more templating agent (hydroxide) compound is typically added to the reaction mixture. If another basic compound is used, the basic compound is preferably an organic base that is free of alkali metals, alkaline earth metals, and the like. The addition of other basic compounds may be needed if the templating agent is added as a salt, e.g., halide or nitrate. Examples of these basic compounds include ammonium hydroxide, quaternary ammonium hydroxides and amines. Specific examples include tetraethylammonium hydroxide, tetrabutylammonium hydroxide, n-butylamine, and tripropylamine.

After the reaction mixture is formed, it is reacted at a temperature and a time sufficient to form a molecular sieve. Typically, the reaction mixture is heated at a temperature of about 100° C. to about 250° C. for a period of about 0.5 hours to about 96 hours in a sealed vessel under autogenous pressure. Preferably, the reaction mixture is heated at a temperature range from about 125° C. to about 200° C., most preferably from about 150° C. to about 180° C. After the desired reaction time, the titanium zeolite is recovered.

Suitable zeolite recovery methods include filtration and washing (typically with deionized water), rotary evaporation, centrifugation, and the like.

The titanium zeolite useful in the invention preferably is of the class of molecular sieves commonly referred to as titanium silicalites, particularly "TS-1" (having an MFI topology analogous to that of the ZSM-5 aluminosilicate zeolites), "TS-2" (having an MEL topology analogous to that of the ZSM-11 aluminosilicate zeolites), and "TS-3" (as described in Belgian Pat. No. 1,001,038). Titanium containing molecular sieves having framework structures isomorphous to zeolite beta, mordenite, ZSM-48, ZSM-12, and MCM-41 may be used in the process of invention.

A binder such as silica, alumina, silica alumina, kaolin and the like can be incorporated in the final catalyst.

The noble metal source comprises a compound or complex of palladium, platinum, gold, silver, iridium, rhenium, ruthenium, osmium, nickle, or mixtures thereof. Palladium, platinum, and gold are particularly desirable; palladium is most preferred. There are no particular restrictions regarding the choice of noble metal compound or complex used as the source of the noble metal. For example, suitable compounds for such purpose include the nitrates, sulfates, halides (e.g., chlorides, bromides), carboxylates (e.g., acetate), and amine complexes of noble metals, as well as compounds containing a mixture of such ligands.

The typical amount of noble metal present in the noble metal-containing titanium zeolite will be in the range of from about 0.001 to 10 wt %. The noble metal is suitably incorporated into the zeolite by ion-exchange with, for example, a tetraammine palladium salt such as tetraammine palladium dinitrate, dihalide or sulfate.

Reaction conditions which are employed are generally known.

The epoxidation is carried out in the liquid phase, and it is advantageous to work at elevated pressure of 1-100 bars gauge. Suitable solvents used in catalyst preparation and in the epoxidation include, but are not limited to, lower aliphatic alcohols such as methanol, ethanol, isopropanol, and tert-butanol or mixtures thereof, and water. Fluorinated alcohols can be used. It is also possible to use mixtures of the cited alcohols with water. Methanol and methanol/water mixtures are preferred. Supercritical carbon dioxide solvent can also be used. Additional solvent can be added before or during epoxidation to improve process results.

Epoxidation according to the invention is carried out at a temperature effective to achieve the desired propylene epoxidation, preferably at temperatures in the range of 0-125° C., more preferably 20-80° C. The reaction is carried out at elevated pressures not to exceed about 100 bars gauge, preferably in the range 2-80 bars gauge.

As the carrier gas, inert gases such as helium, neon, argon, krypton and xenon are suitable as well as nitrogen and carbon dioxide. Saturated hydrocarbons with 1-8, especially 1-6, and preferably with 1-4 carbon atoms, e.g., methane, ethane, propane and n-butane, are also suitable. Nitrogen and saturated $C_1$-$C_4$ hydrocarbons are the preferred carrier gases. Mixtures of the carrier gases can also be used.

A further consideration is the provision of high oxygen to hydrogen ratios in the reaction liquid as above described. The maximum oxygen concentration is governed by the flammable oxygen composition, i.e. the oxygen concentration in the reaction vapor must be maintained below the level at which flammable or explosive mixtures are formed in order to avoid explosion hazards during operation. Oxygen in excess of that needed for complete reaction is fed at a concentration preferably the maximum amount below that at which flammable mixtures are formed.

The system is regulated to give as high a volume ratio of $O_2/H_2$ as possible in the exit gases. Preferably, this ratio is at least 2/1.

EXAMPLE

In a specific example of the present invention as described in FIG. 1, cylindrical tower reactor 1 is provided which is 20 feet in diameter and 140 feet in height. The diameter is set to give a superficial velocity that would create an expansion of the liquid of 20-30%.

Cooling sections 5, 10, 11 and 12 are provided each having 100 tubes 6 inches ID at 15 inch spacing and being 10 feet high. Five reaction zones, zones A-E, are provided each of which is 16 feet high.

Perforated plate 22 is provided just above the main vapor inlet. The inlet vapor comprised of propylene, oxygen and hydrogen passes through the perforations 23 in plate 22 and is finely distributed in the form of small bubbles in reaction zone A.

Figure 2:
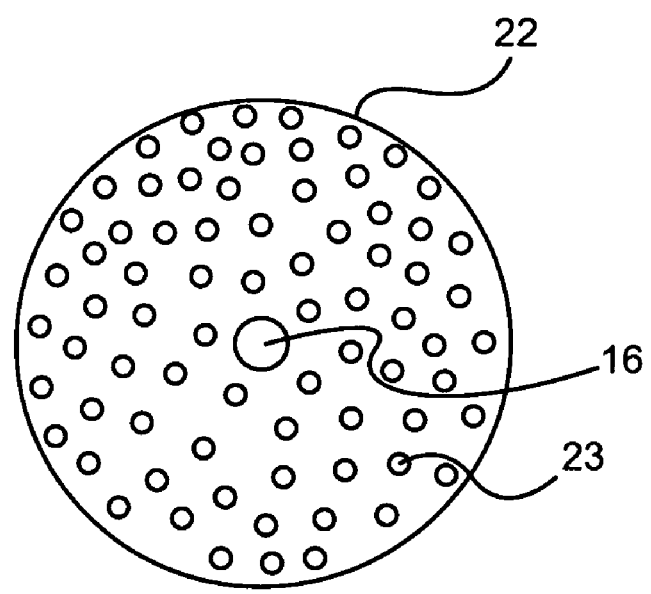
FIG. 2 illustrates the perforated plate through which the feed gases pass.

FIG. 2 illustrates in greater detail the configuration of plate 22. Plate 22 has a plurality of holes or perforations 23 through which the reaction gases pass. It is important that these perforations be no larger in diameter than 1 mm preferably no larger than 0.5 mm in diameter to create proper bubble size and bubble populations. The number of holes should be set to give a gas velocity through the holes of 20 to 50 ft/sec, sufficient to create distinct streams of bubbles that do not coalesce.

In an illustrative practice of the invention, propylene oxide is prepared by the reaction of propylene, oxygen, and hydrogen using a palladium containing TS-1 catalyst (0.1 wt % Pd). Before feeding reagents to the reactor, the reactor is filled from the top with 900,000 lbs. of 10% catalyst in a solvent comprised of 75% by wt. methanol and 25% by wt. water. A small amount of inert gas is fed to the bottom to prevent backflow of the slurry below the perforated plate 22. A feed gas mixture of 5% $H_2$, 10% oxygen, 15% propylene, with the balance methane, is fed below the plate 22 at a rate of 400,000 lb/hr. Solvent is fed above the plate via line 4 at the rate of 140,000 lb/hr.

The feed gases pass through apertures 23 in perforated plate 22 at a velocity of 40 ft/sec. Liquid expansion is 20 vol. %.

Plate 22 has 2,000,000 apertures 23 each of which is 0.5 mm in diameter at 7.5 mm spacing.

As the slurry and feed gases pass upwardly through reaction zone A, the feed gases react to form propylene oxide. Zone A is kept at a temperature of 66° C. by feeding cold solvent thereto, and about 10% of the feed propylene is converted in zone A to propylene oxide.

The reaction slurry and gases pass upwardly through the 6 inch ID cooling tubes 6 in indirect heat exchange with cooling water which is introduced via line 8. In cooling zone 5, the reaction mixture slurry and gases are cooled by about 10 degrees C.

The cooled slurry and the reaction gases pass to reaction zone B wherein the reaction to form propylene oxide is continued. Solid catalyst entrained from Zone A passes via line 16 to the bottom of zone A.

In zone B additional production of propylene oxide takes place and the reaction materials pass upwardly through cooling zone 10 via tubes 6. In zone 10 the reaction exotherm is again removed by indirect heat exchange water introduced via line 20 and removed via line 21, the reaction mixture temperature being reduced from 60 to 50° C.

The reaction slurry mixture passes to reaction zone C where further reaction takes place, thence to cooling zone 11 where the reaction exotherm is removed, thence to reaction zone D, cooling zone 12, and finally to reaction zone E.

From reaction zone E, the reaction slurry is passed through filter tubes 13 and the liquid mixture is recovered via line 14 and passed to appropriate separation means for recovery of product propylene oxide and recycle of solvent (not shown).

In each of the reaction zones, solid catalyst which is entrained is returned via tube 16 to the next lower reaction zone for further use.

The following table shows the reaction liquid composition in each of the five reaction zones.

TABLE 1

| | Percent Composition by Weight | | |
|---|---|---|---|
| Zone | Propylene Oxide | Propylene | Solvent & Others |
| A | 2 | 1.75 | 96.25 |
| B | 4 | 1.70 | 94.30 |
| C | 6 | 1.65 | 92.35 |
| D | 8 | 1.60 | 90.40 |
| E | 10 | 1.5 | 88.45 |

For selectivities purposes, it is important to maintain lower propylene oxide concentrations in the earlier reaction zones in order to minimize ring opening.

The overall selectivity of propylene reacted to propylene oxide is 85%. Vapors exiting the reactor via line 15 comprise by volume 8% $O_2$, 2.5% $H_2$, 13% propylene, 74.5% methane, and 2% others.

We claim:

1. A process for producing propylene oxide comprising reacting hydrogen, oxygen and propylene in the presence of a solid catalyst and a solvent in a series of separate reaction zones of a tower reactor and removing the exothermic heat of reaction by indirect heat exchange in cooling zones of the tower reactor located between consecutive reaction zones, wherein the solvent is selected from the group consisting of an lower aliphatic alcohol, water, and mixtures thereof.

2. The process of claim 1 wherein the solvent is water or a mixture of methanol and water.

3. The process of claim 1 wherein the hydrogen, oxygen and propylene are introduced as diffused fine bubbles by passing through a perforated plate having holes 0.5-1 mm in diameter and spaced 5 to 10 mm apart.

4. The process of claim 1 wherein the catalyst is a noble metal promoted TS-1.

* * * * *